(12) United States Patent
Tsubooka

(10) Patent No.: US 6,601,240 B2
(45) Date of Patent: Aug. 5, 2003

(54) GOGGLES

(75) Inventor: Toru Tsubooka, Sakurai (JP)

(73) Assignee: Yamamoto Kogaku Co., Ltd., Osaka (JP)

( * ) Notice: Subject to any disclaimer, the term of this patent is extended or adjusted under 35 U.S.C. 154(b) by 0 days.

(21) Appl. No.: 09/790,024

(22) Filed: Feb. 21, 2001

(65) Prior Publication Data
US 2001/0029623 A1 Oct. 18, 2001

(30) Foreign Application Priority Data

Feb. 22, 2000 (JP) .................................. 2000-077274

(51) Int. Cl.[7] .................................................. A61F 9/02
(52) U.S. Cl. ......................................................... 2/436
(58) Field of Search ............................. 2/436, 437, 435

(56) References Cited

U.S. PATENT DOCUMENTS

| | | | | |
|---|---|---|---|---|
| 2,388,205 A | * | 10/1945 | Bernheim et al. | 2/437 |
| 3,000,011 A | * | 9/1961 | Sterne et al. | 2/436 |
| 3,368,221 A | * | 2/1968 | Anderson | 2/437 |
| 3,708,224 A | * | 1/1973 | Lindblom | 2/437 |
| 4,443,893 A | * | 4/1984 | Yamamoto | 2/171.3 |
| 5,689,834 A | * | 11/1997 | Wilson | 2/435 |
| 5,711,035 A | * | 1/1998 | Haslbeck | 2/436 |
| 5,867,841 A | * | 2/1999 | Chiang | 2/436 |
| 6,009,564 A | | 1/2000 | Moritz et al. | |
| 6,138,286 A | * | 10/2000 | Robrahn et al. | 2/426 |

FOREIGN PATENT DOCUMENTS

| | | |
|---|---|---|
| DE | 30 05 048 | 11/1980 |
| DE | 195 00 956 | 7/1996 |
| FR | 1 376 188 | 10/1964 |
| FR | 2805155 | * 8/2001 |
| GB | 2173318 | * 10/1986 |
| JP | 2001-231905 | * 8/2001 |
| WO | WO 97 06759 | 2/1997 |
| WO | 97/06759 | * 2/1997 |

* cited by examiner

Primary Examiner—Rodney M. Lindsey
(74) Attorney, Agent, or Firm—Koda & Androlia

(57) ABSTRACT

Goggles include a goggle frame, a goggle lens to be detachably fitted in a groove formed on the inner peripheral portion of the goggle frame. The goggles are provided with a plurality of vent holes in an upper area in the goggle lens. The vent holes located on the both sides are made larger than those in the center.

12 Claims, 7 Drawing Sheets

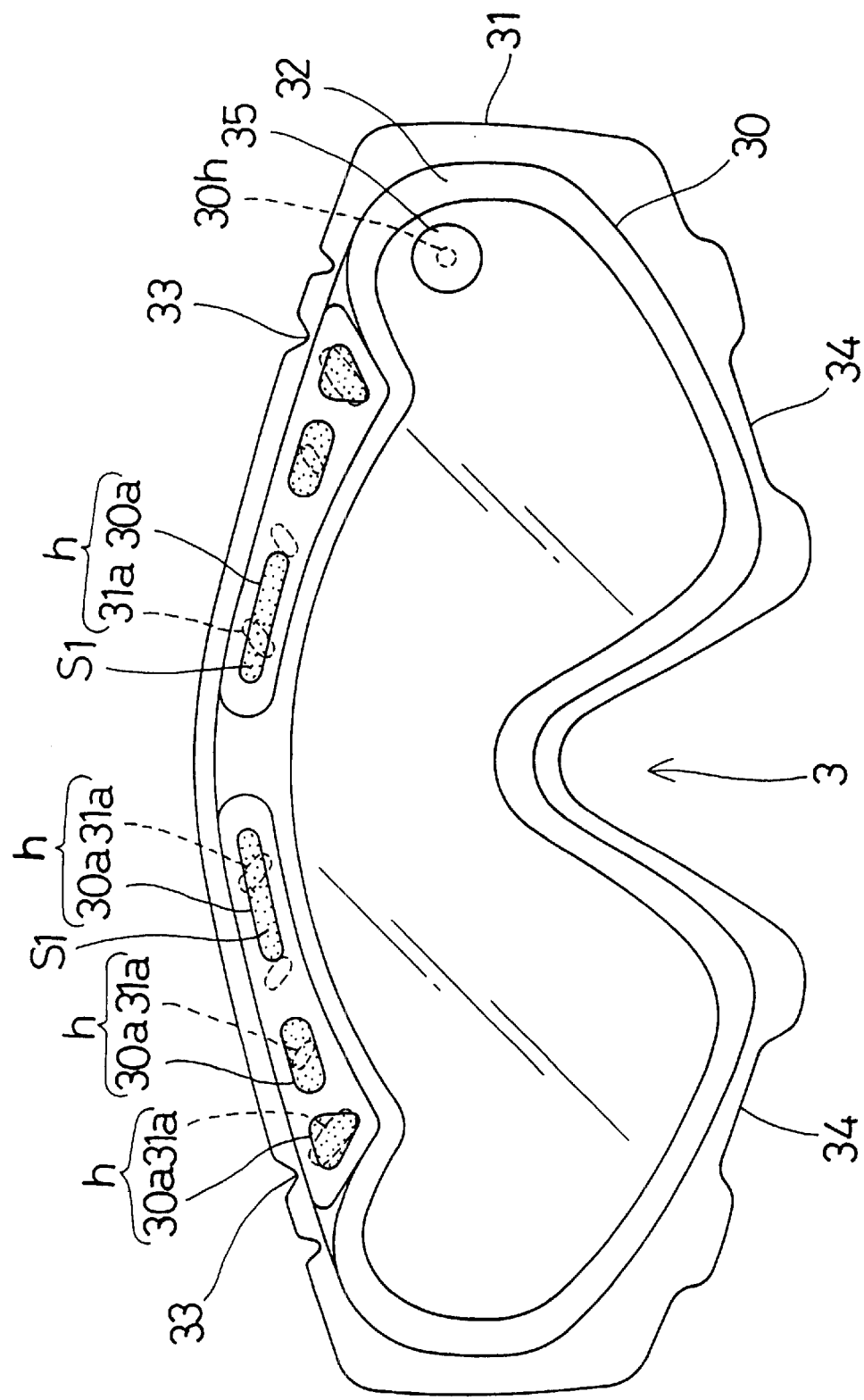

GOGGLES

FIELD OF THE INVENTION

The present invention relates to goggles, more particularly relates to goggles used for skiing and snowboarding.

PRIOR ART

Goggles of this type usually have ventilation sections to prevent inner surfaces of goggle lenses from becoming clouded up with a skier's body temperature, sweating or the like. However, since the skier's cheekbones and their neighborhood become most closer to the inner surfaces of the goggles, the portions of goggle lenses corresponding to them (or both side portions of the goggles) are often clouded up. In view of this, goggles with ventilation sections having a plurality of vent holes above the goggle lenses have recently become available in the market.

However, all the plural vent holes of these conventional goggles are the same in size, or the central vent holes are formed smaller than the side vent holes. Consequently, if such goggles are used in today's skiing or the like which requires a large quantity of motion, a sufficient anti-fog effect cannot necessarily be obtained at the both side portions of the goggles.

Therefore, the field of manufacturing and selling goggles of this type has been focusing on improving goggles which provides a sufficient anti-fog effect even at the both side portions of goggle lenses.

SUMMARY OF THE INVENTION

It is, therefore, an object of the present invention to provide goggles which produce a sufficient anti-fog effect even at the both side portions of goggle lens(es).

Goggles according to the present invention include a goggle frame and a goggle lens detachably fitted into a groove formed on the inner peripheral portion of the goggle frame. The goggles have a plurality of vent holes above the goggle lens, and vent holes located on the both sides are formed larger than those in the center.

Goggles according to the present invention include a goggle frame and a goggle lens detachably fitted into a groove formed on the inner peripheral portion of the goggle frame. The goggles have a plurality of vent holes above the goggle lens, and vent holes provided at positions corresponding to areas above a wearer's cheekbones and their neighborhood are formed larger than vent holes provided at the other positions.

The vent holes of the goggles of the present invention may be closed up by filters.

The goggles of the present invention may have a gap between the bottom of the groove and the outer peripheral edge of the goggle lens and near the vent holes on the both sides so as to allow inside and outside of the goggle lens to communicate through the gap.

The goggles according to the present invent may include an air inducing opening at least on a front wall out of the front and rear walls constituting the groove and the opening may communicate to the gap.

The embodiments of goggles of the invention stated above will be described below with reference to the accompanying drawings.

BRIEF DESCRIPTION OF THE DRAWINGS

FIG. 7 is a rear view of one goggle lens used in the goggles.

DESCRIPTION OF THE EMBODIMENTS OF THE INVENTION

Figure 1:
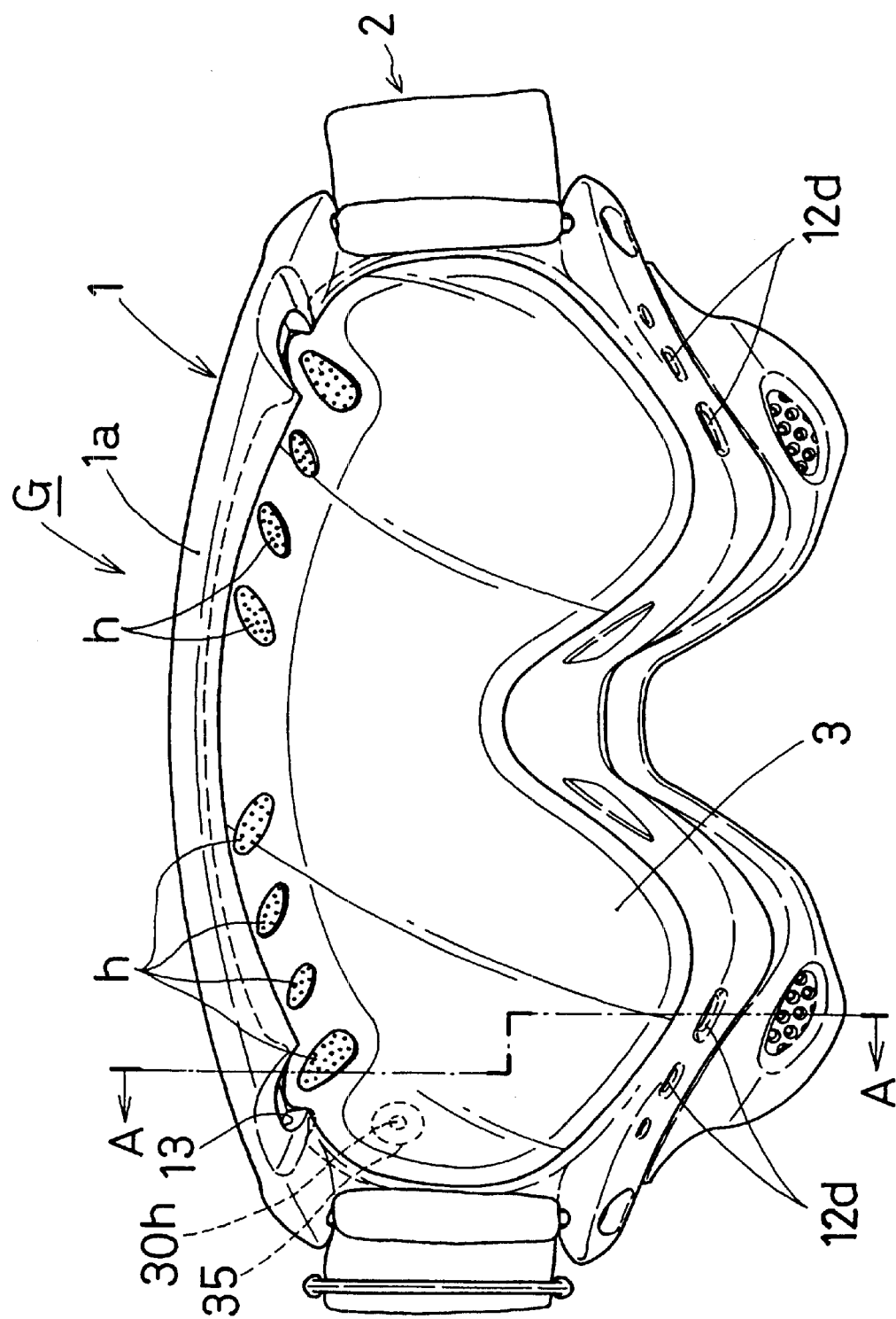
FIG. 1 is a front view of goggles in one embodiment of the present invention.
Figure 2:
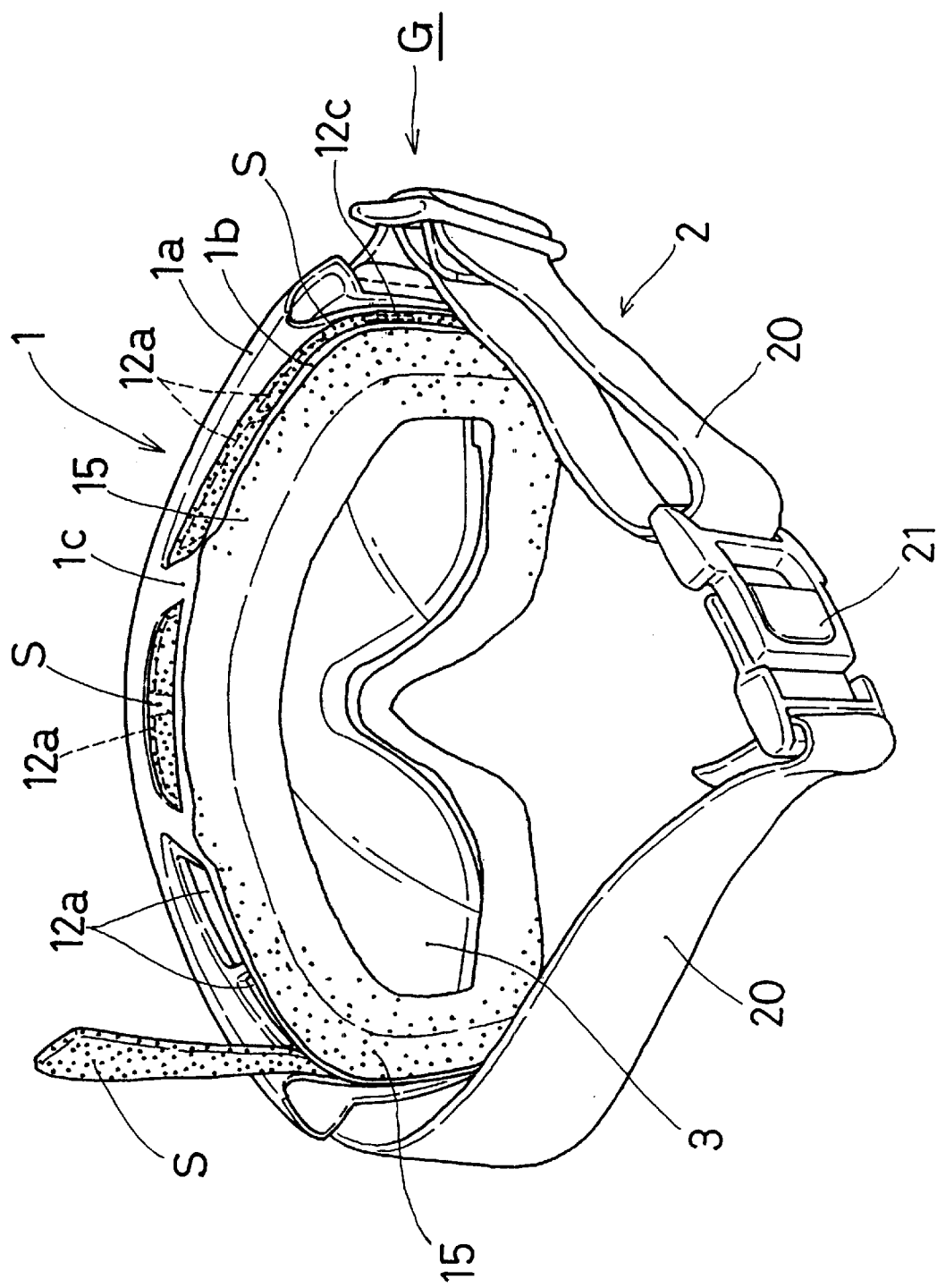
FIG. 2 is a rear view of the goggles.

FIG. 1 is a front view of skiing goggles G. FIG. 7 is a view of a goggle lens 3 used in the goggles G, which is seen from a side of an inner lens plate 30. As shown in FIGS. 1 and 2, the goggles G include a goggle frame 1, an expandable, elastic band 2 coupled to the goggle frame 1, and a goggle lens 3 detachably fitted into the goggle frame 1.

Figure 3:
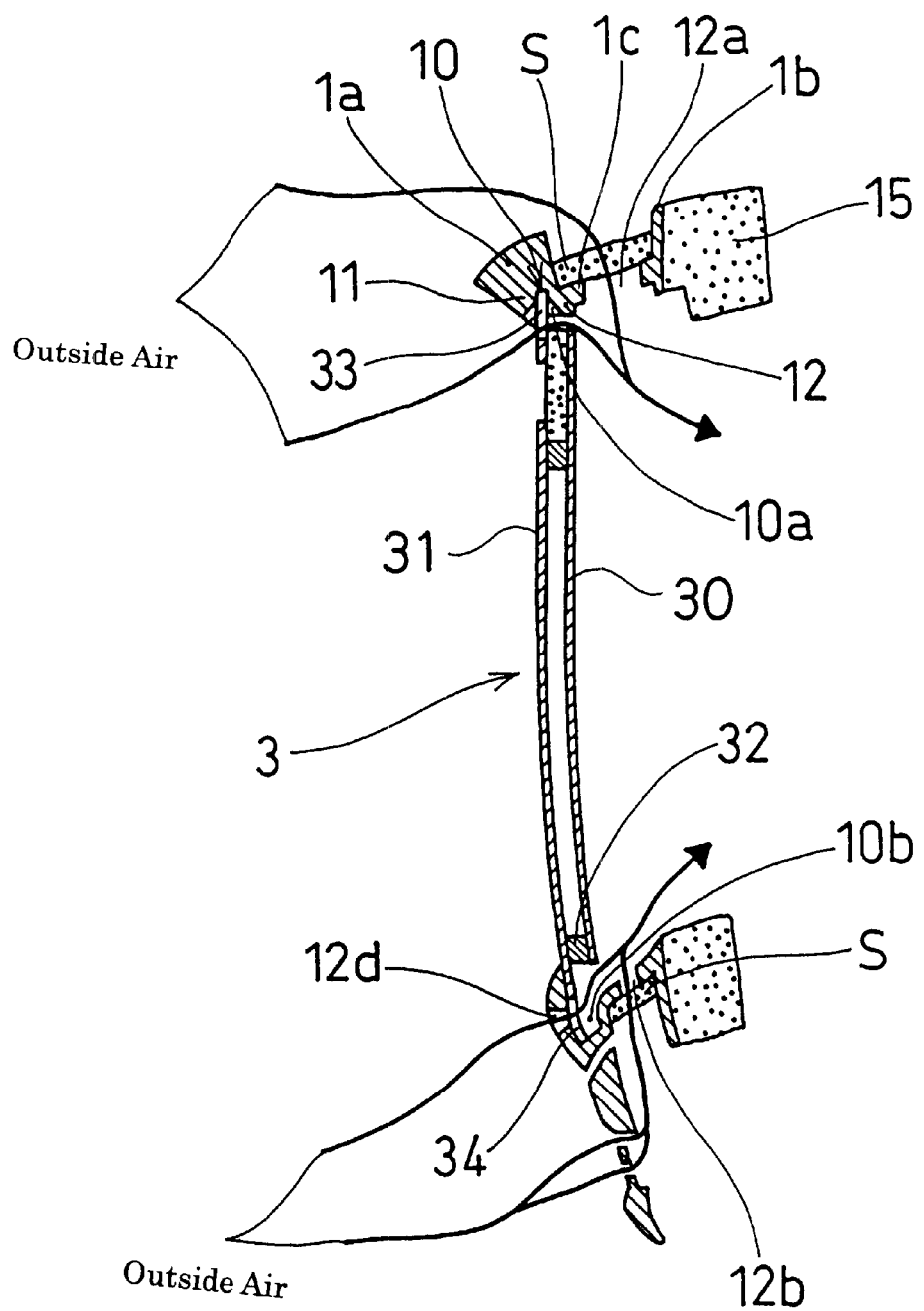
FIG. 3 is a cross-sectional view taken along line A—A of FIG. 1.

The goggle frame 1 is made of soft material such as an elastic synthetic resin, rubber or the like. As shown in FIGS. 2 and 3, the goggle frame 1 includes a lens fitting edge 1a, a face abutment section 1b and a peripheral wall section 1c connecting the lens fitting edge 1a to the face abutment section 1b. The goggle lens 3 is detachably fitted into the lens fitting edge 1a.

Figure 4:
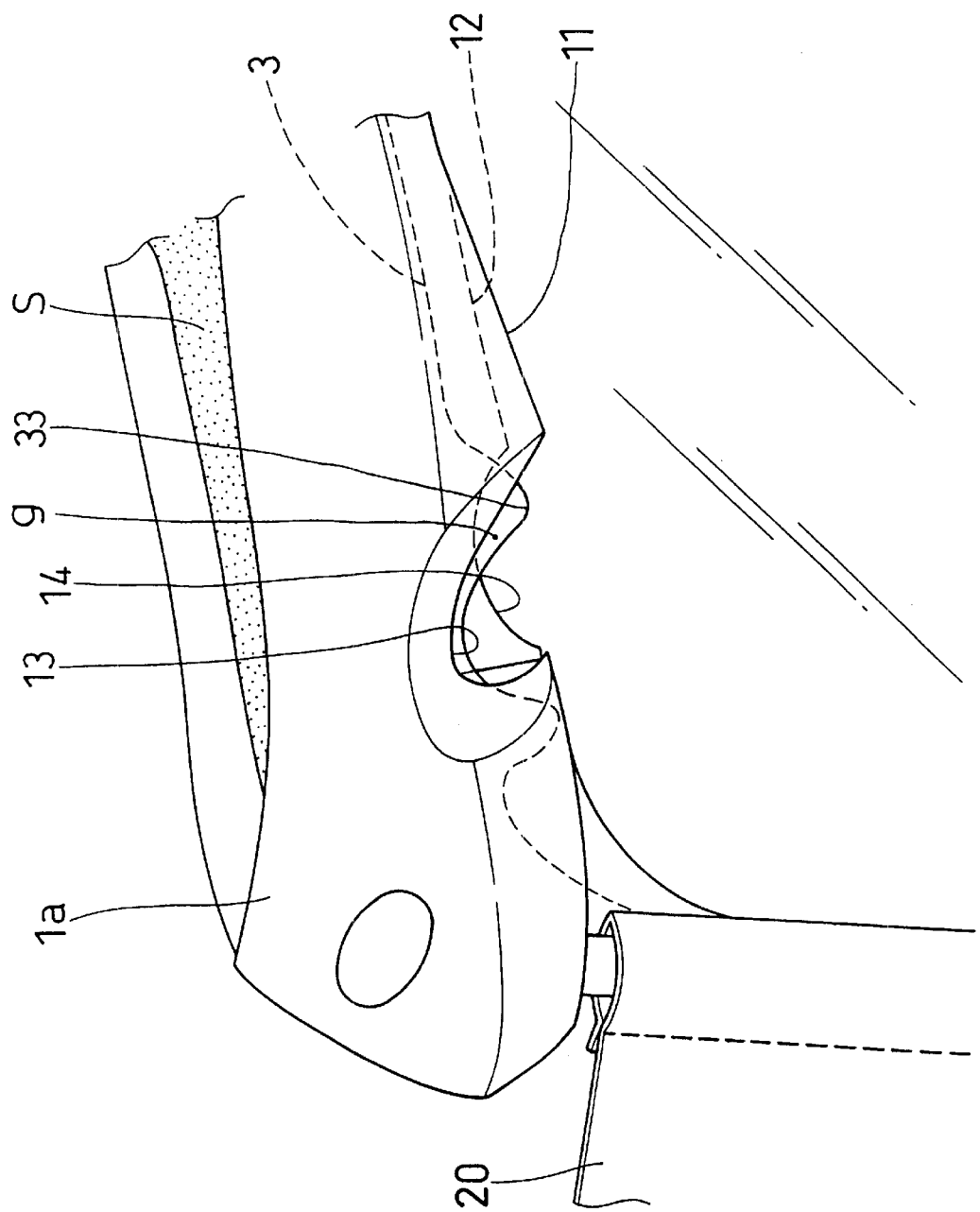
FIG. 4 is an enlarged view showing opening portions formed on the goggle frame of the goggles and the vicinity.
Figure 5:
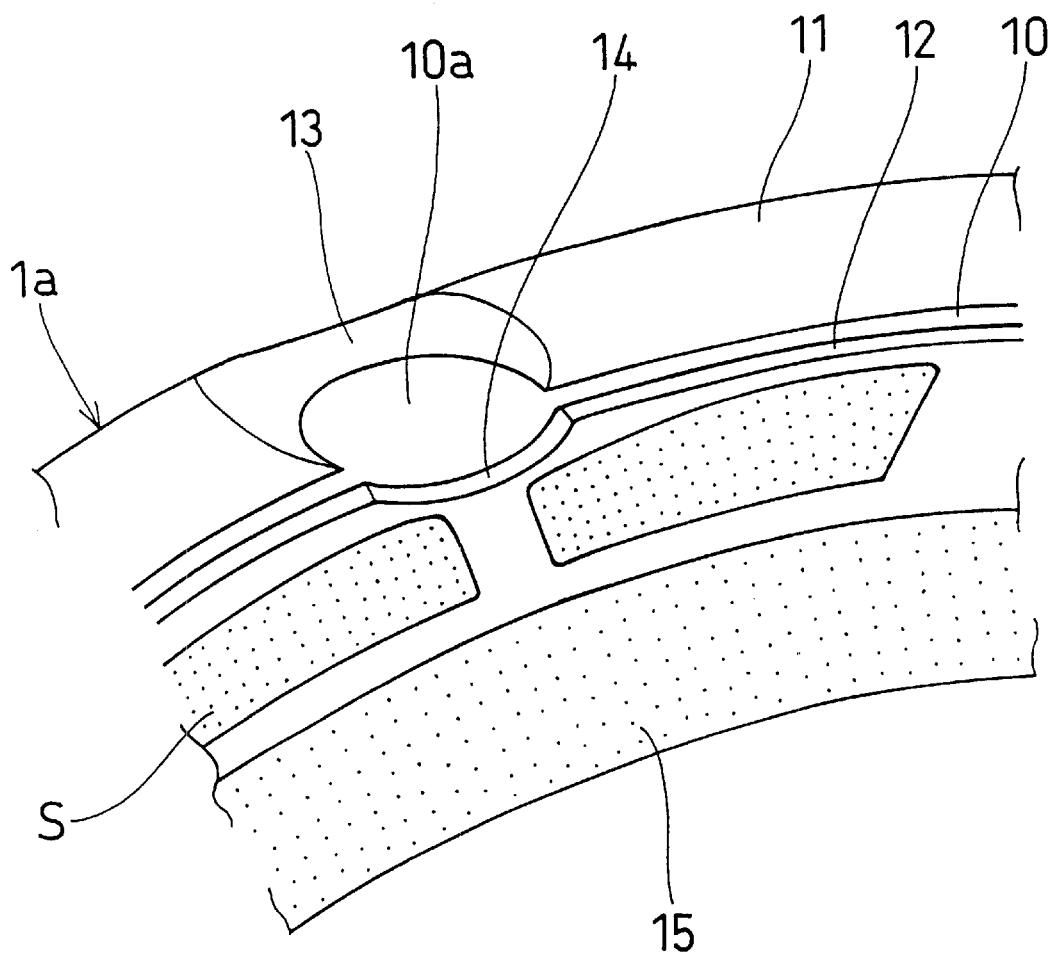
FIG. 5 is a view of the opening portions on the goggle frame and the vicinity seen from below.
Figure 6:
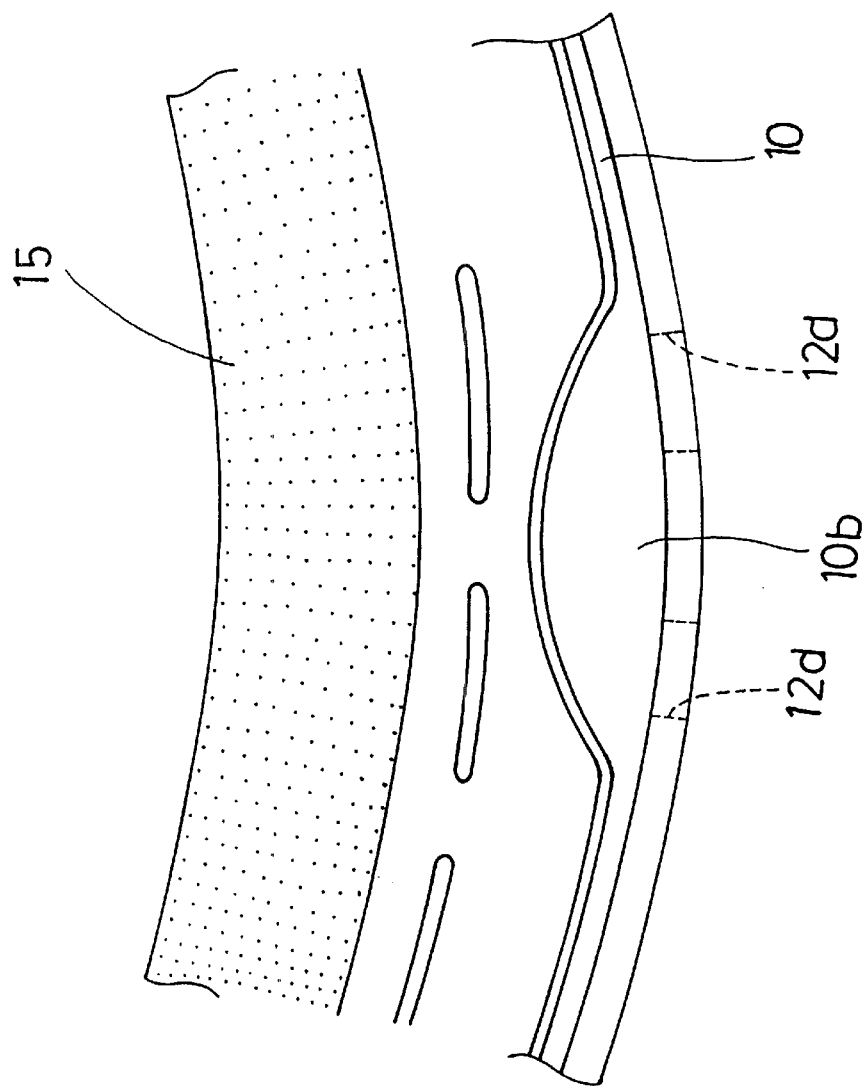
FIG. 6 is a view of a ventilation formed on the lower portion of the goggle frame and the vicinity, which is seen from above.

As shown in FIG. 3, the lens fitting edge 1a is provided with a groove 10 in which an outer peripheral edge of the goggle lens 3 is received. The groove 10 is constituted with a front wall 11 and a rear wall 12. As shown in FIG. 4, air vent openings 13 and 14 are provided on the front and rear walls 11, 12 and at the both lateral side portions of the goggles, and they oppose each other. As shown in FIGS. 4 and 5, the openings 13 and 14 are respectively formed out of notches, and the width of the groove 10 close to the portions on which the openings 13 and 14 are formed, is set wider (this wider portion of the groove 10 are indicated by 10a). Further, as shown in FIG. 1, ventilation sections 12d are formed by providing holes in a constitution wall of the lower front portion of the lens fitting edge 1a. As shown in FIG. 6, the width of the groove 10 close to the ventilation sections 12d is set wider (this wider portion of the groove 10 are indicated by 10b).

The abutment section 1b, as shown in FIGS. 2 and 3, is provided with a close contact material 15 such as sponge or monte plane in order to give confortable close fitting to a wearer's face.

The peripheral wall section 1c, as shown in FIGS. 2 and 3, is provided with ventilation sections 12a, 12b and 12c having holes on the vertical and horizontal constitution walls of the section 1c. The ventilation sections 12a, 12b and 12c are respectively designed to be closed by and covered with thin sponge plates S. The reason for closing and covering the ventilation sections 12a, 12b and 12c by the sponge plates S is to prevent snow and/or dust other than air from entering inside of the goggles.

As shown in FIG. 2, the expandable, elastic band 2 includes band main bodies 20 and 20 respectively attached to the both side ends of the goggle frame 1, and a buckle 21 coupling the band main bodies 20 and 20 together. The band main bodies 20 used here are designed to be expandable.

The goggle lens 3 is shown in FIGS. 3 and 7. The gaggle lens 3 has a double-lens structure in which two inner and outer lens plates 30 and 31 made of transparent or color plastic are put together through a spacing frame 32. Upper area of the gaggle lens 3 is provided with ventilation sections having holes 30a and 31a respectively formed on the inner and the outer lens plates 30 and 31 and sponge plates S1 (or filters) to close and cover the holes 30a and 31a. The surface of the inner lens plate 30 which faces a wearer's face is given anti-fog treatment. On the other hand, the front surface of the outer lens plate 31 is given a so-called UV coat or hard coat so as to avoid ultraviolet rays. In addition, practical vent holes h formed with the holes 30a and 31a and located at the both side portions are made larger than those h in the center.

In this embodiment, the outer peripheral edge of the outer lens plate 31 is fitted into the groove 10. Concave portions 33 are formed at positions corresponding to the openings 13 and 14 and the wider portion 10a of the groove 10, as shown in FIGS. 4 and 5, and concave portions 34 are formed at positions corresponding to the ventilation sections 12d and the wider portion 10b of the groove 10, as shown in FIGS. 3 and 6.

Further, in this embodiment, as shown in FIG. 1, a vent hole 30h is formed in an area near the outer edge of the inner lens plate 30, the area being out of the field of vision. The vent hole 30h is closed by a water-repellant vent sheet 35 which prevents moisture from passing and allows air to pass.

The practical vent holes h formed by the holes 30a and 31a and located at the both side portions are made larger than those h in the center. With this structure, the goggles according to the present invention provides a more sufficient anti-fog effect even on the both lateral sides of the goggle lens 3 compared with the conventional ones.

The concave portion 33 allows to have a gap between the outer peripheral edge of the goggle lens 3 and the bottom of the groove 10, as shown in FIG. 4. In addition, the gap g and the wider portion 10a of the groove 10 allow the openings 13 and 14 to communicate. Thus, outside air flows in inside the goggles along the arrowed route shown in FIG. 3.

Also, the concave portion 34 allows to have a gap between the outer peripheral edge of the goggle lens 3 and the bottom of the groove 10 as shown in FIG. 3. Furthermore, the gap g and the wider portion 10b of the groove 10 allows the ventilation section 12d and inside of the goggles to communicate each other. Consequently, outside air flows in inside the goggles as shown in FIG. 3.

As shown in FIG. 1, the foregoing openings 13 and 14 and the ventilation sections 12d are provided on both lateral sides of the goggle frame 1. Therefore, even when outside air flows in inside of the goggles 1, the goggles provides a sufficient anti-fog effect even at the both side portions of the goggle lens 3.

In the embodiment stated above, the groove 10 is provided with wider portions 10a and 10b. But, if the gap g is large enough, such wider portions 10a and 10b are not necessary.

Furthermore, the constitution of the goggles according to the present invention should not be limited to be applied to skiing goggles but is also applicable to goggles for other purposes.

With the constitution stated above, the present invention can provide goggles which produce a sufficient anti-fog effect even on the both side portions of the goggle lens(es).

What is claimed is:
1. Goggles comprising:
a goggle frame;
a groove including a front wall and a rear wall on an inner peripheral portion of said goggle frame;
a goggle lens detachably fitted into said groove;
a plurality of vent holes provided at an upper area in said goggle lens; and
a gap being provided between a bottom of said groove and an outer peripheral edge of said goggle lens so as to allow inside and outside of said goggle lens to communicate through said gap, said gap being formed near both of said vent holes located on both sides of said goggles.

2. Goggles according to claim 1, wherein an air inducing opening is provided at least on the front wall of said front and rear walls constituting said groove, and said opening communicates to said gap.

3. Goggles according to claim 1, wherein said both of said vent holes located on both sides are made larger than those of said vent holes in a center.

4. Goggles according to claim 2, wherein said both of said vent holes located on both sides made larger than those of said vent holes in a center.

5. Goggles according to claim 1, wherein said both of said vent boles located on both sides ate positioned corresponding to area above a wearer's cheekbones and their neighborhood and formed larger than those of said vent holes provided at other positions.

6. Goggles according to claim 2, wherein said both of said vent holes located on both sides are positioned corresponding to area above a wearer's cheekbones and their neighborhood and formed larger than those of said vent holes provided at other positions.

7. Goggles according to claim 1, wherein said goggle lens has a concave portion at least at a position corresponding to said gap.

8. Goggles according to claim 2, wherein said goggle lens has a concave portion at a position corresponding to said gap.

9. Goggles according to claim 1, wherein said vent hales are filled only with filters.

10. Goggles according to claim 2, wherein said vent holes are filled only with filters.

11. Goggles comprising:
a goggle frame;
a groove constituted with a front wall and a rear wall on an inner peripheral portion of said goggle frame;
a goggle lens detachably fitted into said groove;
a plurality of vent holes provided at an upper area in said goggle lens; and
vent openings provided at least on said front wall of said front and rear walls on both sides of said goggles.

12. Goggles comprising:
a goggle flame;
a groove constituted with a front wall and a rear wall on an inner peripheral portion of said goggle frame;
a goggle lens detachably fitted into said groove;
a plurality of vent holes provided at an upper area in said goggle lens; and
vent openings being provided at least on said front wall of said front and rear walls at positions corresponding to areas above a wearer's cheekbones and their neighborhood.

* * * * *